US012589091B2

(12) United States Patent
Ravindrakumar Jivan

(10) Patent No.: US 12,589,091 B2
(45) Date of Patent: Mar. 31, 2026

(54) TOPICAL FORMULATION COMPRISING SIROLIMUS

(71) Applicant: SODHA PHARMA CONSULTING GMBH, Oberwil (CH)

(72) Inventor: Sodha Ravindrakumar Jivan, Oberwil (CH)

(73) Assignee: SODHA PHARMA CONSULTING GMBH, Oberwil (CH)

( * ) Notice: Subject to any disclaimer, the term of this patent is extended or adjusted under 35 U.S.C. 154(b) by 391 days.

(21) Appl. No.: 18/039,785

(22) PCT Filed: Feb. 9, 2022

(86) PCT No.: PCT/EP2022/053113
§ 371 (c)(1),
(2) Date: Jun. 1, 2023

(87) PCT Pub. No.: WO2022/233468
PCT Pub. Date: Nov. 10, 2022

(65) Prior Publication Data
US 2024/0000757 A1     Jan. 4, 2024

(30) Foreign Application Priority Data
May 5, 2021     (EP) .................................... 21172232

(51) Int. Cl.
| | |
|---|---|
| *A61K 31/436* | (2006.01) |
| *A61K 9/00* | (2006.01) |
| *A61K 47/10* | (2017.01) |
| *A61K 47/14* | (2017.01) |
| *A61K 47/32* | (2006.01) |

(52) U.S. Cl.
CPC .......... *A61K 31/436* (2013.01); *A61K 9/0014* (2013.01); *A61K 47/10* (2013.01); *A61K 47/14* (2013.01); *A61K 47/32* (2013.01)

(58) Field of Classification Search
None
See application file for complete search history.

(56) References Cited

U.S. PATENT DOCUMENTS

2020/0316034 A1* 10/2020 Kaupinen .............. A61K 47/28

OTHER PUBLICATIONS

Bonacucina et. al. "Characterization and Stability of Emulsion Gels Based on Acrylamide/Sodium Acryloyldimethyl Taurate Copolymer" AAPS PharmSciTech, 2009, 10, 2, 368-375. DOI: 10.1208/s12249-009-9218-1 (Year: 2009).*
CAS 56-81-5. CAS Registry File Accessed Sep. 2, 2025 from STN, entered into STN Nov. 16, 1984. (Year: 1984).*

* cited by examiner

Primary Examiner — Jennifer A Berrios
Assistant Examiner — Sophia Reilly
(74) Attorney, Agent, or Firm — Daniel S. Kim

(57) ABSTRACT

The present invention concerns a pharmaceutical composition for topical administration, comprising sirolimus, solvent, thickener and glycol ether. The invention further concerns a pharmaceutical composition for use in the treatment of skin diseases or skin manifestations of diseases, especially of skin manifestations of tuberous sclerosis complex (TSC). The invention further concerns a method for producing a pharmaceutical composition comprising the steps of (i) providing sirolimus and (ii) forming the present composition.

12 Claims, 2 Drawing Sheets

Cumulative release of sirolimus from the 0.4 w/w% sirolimus gel composition according to Example 1 and from the 0.4 w/w% sirolimus petrolatum onitment with time.

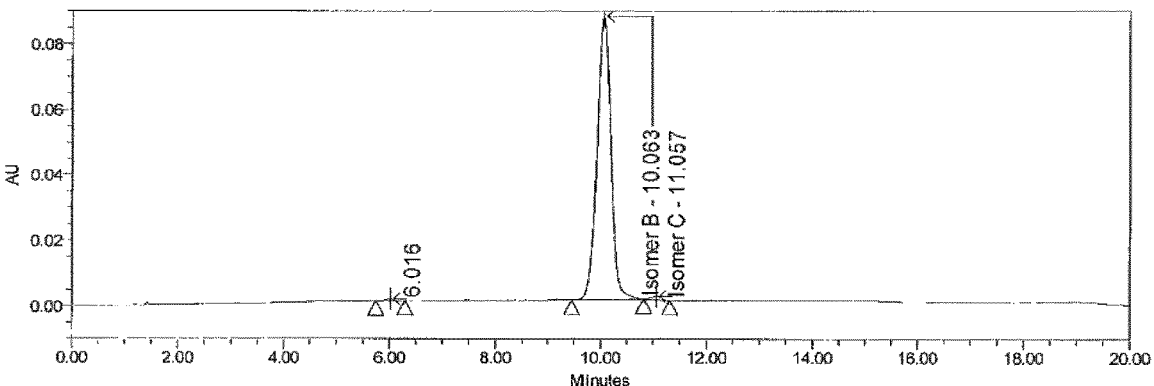
Figure 1: An example of a chromatogram of the standard solution according to the Analytical method 1.
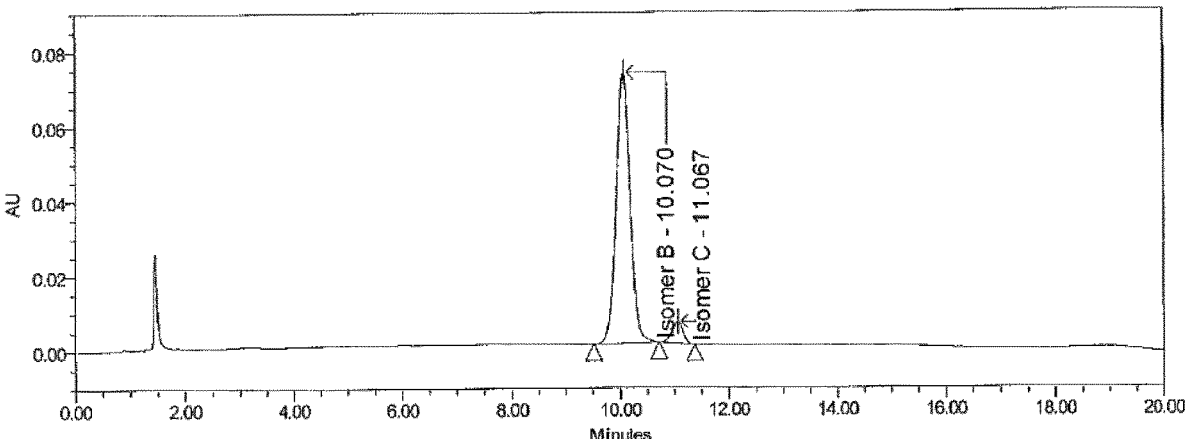
Figure 2: An example of a chromatogram of a sample solution according to the Analytical method 2.

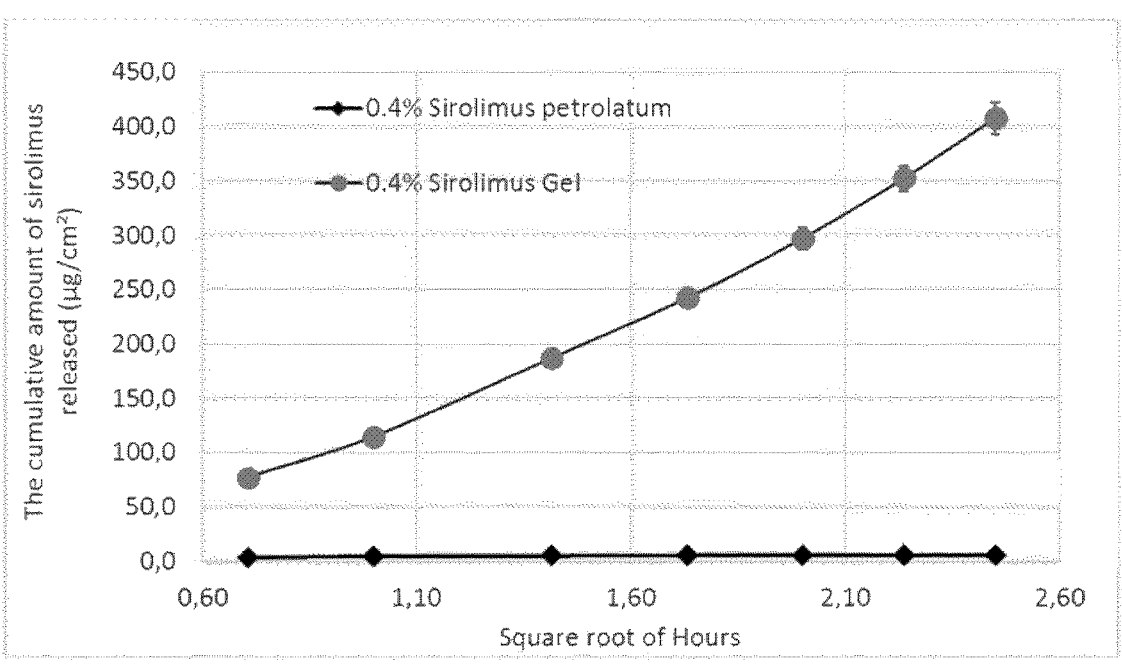

Figure 3: Cumulative release of sirolimus from the 0.4 w/w% sirolimus gel composition according to Example 1 and from the 0.4 w/w% sirolimus petrolatum onitment with time.

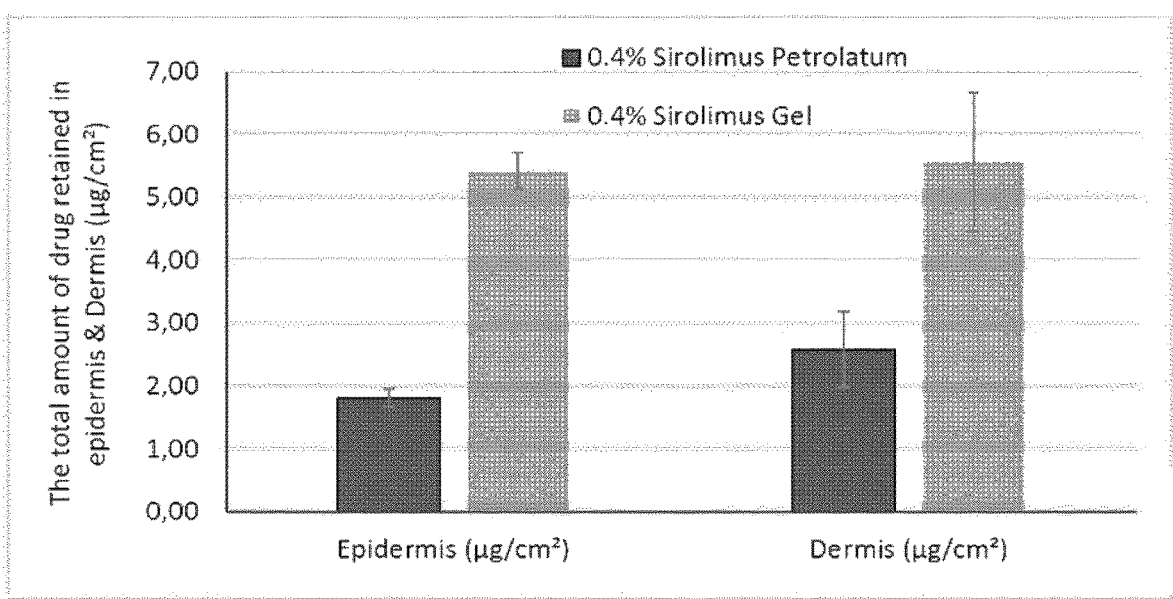

Figure 4: Total amount of sirolimus retained in the epidermis and dermis after 24h exposure to the 0.4 w/w% sirolimus gel composition of Example 1 and the 0.4 w/w% sirolimus petrolatum onitment to human cadaver skin.

TOPICAL FORMULATION COMPRISING SIROLIMUS

The present invention concerns a pharmaceutical composition for topical administration comprising sirolimus, solvent, thickener and glycol ether. The invention further concerns the present pharmaceutical composition for use in treatment of skin diseases or skin manifestations of diseases as well as a method for producing the present pharmaceutical composition.

BACKGROUND SECTION

Sirolimus or rapamycin has been known to be used in treatment of dermatologic conditions such as benign cutaneous tumors, Kaposi sarcoma, inflammatory skin diseases, vascular malformations and skin manifestations of tuberous sclerosis complex (Leducq S. et al.: "A. Topical use of mammalian target of rapamycin inhibitors in dermatology: A systematic review with meta-analysis", J Am Acad Dermatol., March 2019; 80(3), pp. 735-742). Further, US 2013/0317053 A1 and US 2020/0000778 A1 provide lists of skin diseases and skin manifestations for the treatment of which sirolimus can be used. Especially, sirolimus can be used in the treatment of skin manifestations of tuberous sclerosis complex.

Tuberous sclerosis complex (TSC) is an autosomal dominant genetic disease that causes non-cancerous tumors to grow in the brain and on other vital organs such as the kidneys, heart, liver, eyes, lungs and skin. TSC is caused by a mutation of either of two genes, TSC1 and TSC2, which code for the proteins hamartin and tuberin, respectively. These proteins act as tumor growth suppressors, hence as agents regulating cell proliferation and differentiation. A combination of symptoms may include seizures, intellectual disability, developmental delay, behavioral problems, skin abnormalities, lung disease and kidney disease. The skin manifestations of the tuberous sclerosis complex (TSC) may include hypomelanic macules, facial angiofibromas, ungual fibromas also known as Koenen's tumors, fibrous cephalic plaques, shagreen patches, dental enamel pits, intraoral fibromas, etc.

Sirolimus has been used in the systemic treatment of patients with tuberous sclerosis complex (TSC) in an attempt at treating a brain tumor, a kidney tumor and a lung tumor of the patients. Even more, systemic administration of sirolimus has also been used in the treatment of a skin tumor. Although the size of the skin tumor decreased during the systemic administration of sirolimus, it occurred that the tumor increased in size when the systemic therapy was discontinued. Hence, in order to systemically treat skin tumors, it was necessary to systemically administer sirolimus for a long period of time. However, such a long systemic treatment with sirolimus is prone to disadvantageous side effects occurring during or after the treatment.

Further, it has been tried to treat skin manifestations of tuberous sclerosis complex (TSC) with topical formulations comprising sirolimus. It is well known that for an efficient percutaneous absorption of a compound, the molecular weight of a compound should be preferably less than 500 Dalton. As the molecular weight of sirolimus is 914 Dalton, the composition of a topical pharmaceutical formulation comprising sirolimus is crucial for providing sufficient percutaneous absorption. In US 2013/0317053 A1 in-vitro absorption tests of aqueous gel and ointment compositions comprising 0.2 wt. % to 1.0 wt. % of sirolimus were provided, indeed indicating sufficient absorption and accumulation of sirolimus in the dermis and epidermis. Further, these compositions also show a therapeutic effect in treatment of angiofibroma and vitiligo and reduce the concentration of vascular endothelial growth factor (VEGF) in skin tumor tissue. However, these compositions are considered as improvable with regard to their stability.

Moreover, in US 2020/000778 A1 several compositions and methods for topical delivery of mTOR inhibitors were proposed. The compositions provided therein comprise one or more mTOR inhibitors, one or more solvents, one or more gelling agents and one or more antioxidants. The typical amount of rapamycin (the mTOR inhibitor in US 2020/000778) in the compositions for topical delivery is in the range of 1 wt. % to 4.59 wt. %, based on the total weight of the composition. However, also these compositions seem to be improvable with respect to the side effects related to a high amount of sirolimus.

US 2020/316034 relates to compositions and methods for the topical delivery of mTOR inhibitors. For example, said document describes an anhydrous composition that includes one or more mTOR inhibitors, one or more solvents, one or more gelling agents, and one or more antioxidants. Further, the document relates to methods to treat skin disorders using such compositions. WO 2020/175131 A1 relates to the treatment of vascular abnormalities (vascular deformation and vascular tumor) through transdermal or trans-mucosal membrane application of at least one selected from the group consisting of sirolimus and a sirolimus derivative, wherein the sirolimus derivative may be everolimus, temsirolimus, ridaforolimus, zotarolimus, etc. WO 2020/184128 relates to a locally applied, external preparation containing at least one selected from the group consisting of sirolimus and sirolimus derivatives, and diethylene glycol ether. The external preparation is described to be a formulation enabling the penetration of sirolimus or sirolimus derivative into the epidermis, as well as accumulation in the dermis.

Usually, skin manifestations of patients with tuberous sclerosis complex undergo treatment with topical pharmaceutical compositions of sirolimus extending over a longer period of time. Therefore, it is beneficial if sirolimus remains stable in the pharmaceutical composition, the longer the better. The constitution (excipients and their respective amounts) of the pharmaceutical composition is intrinsically linked to the stability of sirolimus in the composition. Hence, an advantageous stability of sirolimus can be achieved by an appropriate selection of the pharmaceutical composition.

For achieving a suitable therapeutic effect, an appropriate permeability and distribution of sirolimus in skin layers is essential, wherein it is known that the permeability and distribution of sirolimus in skin layers are also intrinsically linked to viscous properties of the pharmaceutical composition. In the art, pharmaceutical compositions of sirolimus in petrolatum have been used in the treatment of skin diseases and skin manifestations of diseases (Foster et al.: "Topical 0.1% rapamycin for angiofibromas in paediatric patients with tuberous patients with tuberous sclerosis: a pilot study of four patients", Australas J Dermatol 2012; 53(1), pp. 52-56). However, the permeability and distribution of sirolimus in skin layers appear to be in need of improvement in said petrolatum compositions.

OBJECTS OF THE INVENTION

An object of the present invention is to overcome drawbacks of the prior art. Inter alia, it is an object of the present invention to provide a pharmaceutical composition for topical administration comprising sirolimus which can be used for the treatment of skin diseases or skin manifestations of diseases such as skin manifestations of tuberous sclerosis complex (TSC).

It is an object of the present invention to provide a pharmaceutical composition comprising sirolimus which can be used in a long-term treatment with none or significantly reduced systemic side effects related to the use of sirolimus.

It is an object of the present invention to provide a pharmaceutical composition comprising sirolimus wherein said composition ensures the deposition of suitable therapeutic amounts of sirolimus in the affected skin layers such as epidermis and dermis and/or to avoid the entering of too high amounts of sirolimus into the systemic blood flow. In other words, it is an object of the present invention to provide a pharmaceutical composition comprising sirolimus to achieve an advantageous steady-state distribution of sirolimus in the affected skin layers and thereby achieving a therapeutic effect with an advantageously low amount of applied sirolimus.

Further, it is an object to provide a pharmaceutical composition comprising sirolimus with a permeability enabling a suitable amount of sirolimus content to permeate into the skin layers. In particular, a sufficient amount should permeate into the skin layer(s), but it should be avoided that too high amounts of sirolimus permeate across the skin layer(s).

Even further, it is an object to provide a pharmaceutical composition comprising sirolimus which enables the reduction of the number of applications without negatively affecting the therapeutic effect to achieve an advantageous patient compliance.

It is an object of the present invention to provide a pharmaceutical composition for topical administration comprising sirolimus with advantageous stability.

It is an object of the present invention to provide a method for producing a pharmaceutical composition for topical administration comprising sirolimus.

The present invention has unexpectedly solved at least one of the above objects by a new pharmaceutical composition for topical administration comprising sirolimus, solvent, thickener and glycol ether.

Thus, a subject of the present invention is a new pharmaceutical composition suitable for topical administration comprising sirolimus a), solvent b), thickener c) and glycol ether d), wherein the content of thickener c) is between 0.05 and 10.0 wt. %, based on the total weight of the composition, and wherein the content of glycol ether d) is between 0.05 and 10.0 wt. %, based on the total weight of the composition.

In an embodiment of the invention, the content of sirolimus a) is between 0.05 and 5.0 wt. %, based on the total weight of the composition.

In another embodiment of the invention, solvent b) comprises propylene glycol and glycerin.

In another embodiment of the invention, thickener c) comprises acrylamide/sodium acryloyldimethyl taurate copolymer.

In another embodiment of the invention, glycol ether d) is diethylene glycol ethyl ether.

In another embodiment of the invention, the pharmaceutical composition further comprises antioxidant e).

In another embodiment of the invention, the content of antioxidant e) is between 0.005 and 0.2 wt. %, based on the total weight of the composition.

In another embodiment of the invention, antioxidant e) is propyl gallate.

In another embodiment of the invention, the pharmaceutical composition is stable at 2° C. to 8° C. for 1 year.

A further subject of the present invention is the present composition for use in the treatment of skin diseases or skin manifestations of diseases, preferably skin diseases or skin manifestations of diseases such as genodermatoses, skin manifestations resulting from vascular conditions, malignant and benign skin tumors, skin manifestations of auto-immune/inflammatory conditions, skin manifestations of infection and infestation, skin manifestations of miscellaneous causes and/or skin manifestations of tuberous sclerosis complex (TSC).

In an embodiment of the invention, skin manifestations of tuberous sclerosis complex (TSC) comprise facial angiofibroma, hypomelanic macules, ungual fibromas, fibrous cephalic plaques and/or shagreen patches.

In another embodiment of the invention, the dosing scheme is twice daily, once daily, every second day and/or once weekly.

Another subject of the present invention is a method of producing a pharmaceutical composition of the invention and its embodiments, wherein the method comprises the steps of (i) providing sirolimus a), and (ii) forming the present composition.

BRIEF DESCRIPTION OF DRAWINGS

FIG. 1: An example of a chromatogram of the standard solution according to Analytical method 1.

FIG. 2: An example of a chromatogram of a sample solution according to Analytical method 2.

FIG: 3: Cumulative release of sirolimus from the 0.4 w/w % sirolimus gel composition according to Example 1 and from the 0.4 w/w % sirolimus petrolatum ointment with time.

FIG. 4: Total amount of sirolimus retained in the epidermis and dermis after 24 h exposure to the 0.4 w/w % sirolimus gel composition of Example 1 and the 0.4 w/w % sirolimus petrolatum ointment to human cadaver skin.

DETAILED DESCRIPTION

The present pharmaceutical composition is suitable for topical administration. In line with the present application, topical administration means application to body surfaces such as the skin or mucous membranes to treat ailments via a large range of classes including creams, foams, gels, lotions and ointments. Many topical administrations are epicutaneous, meaning that they are applied directly to the skin. Topical administrations may also be inhalational, such as asthma administrations, or applied to the surface of tissues other than the skin, such as eye drops applied to the conjunctiva, or ear drops placed in the ear, or medications applied to the surface of a tooth. In the present application, topical administration is preferably referred to as application on the skin.

In some embodiments, the pharmaceutical composition for topical administration is a cream, a foam, a gel, a lotion, an ointment, a paste, a powder, a shake lotion, a tape, a tincture, a topical solution or a transdermal patch. Preferably, in some embodiments, the pharmaceutical composition is a cream, a foam, a gel, a lotion or an ointment. More preferably, in some embodiments, the pharmaceutical composition is a cream or a gel. In particular, the pharmaceutical composition is a gel.

A gel is referred to as a nonfluid colloidal network or polymeric network that is expanded throughout its whole volume by a fluid. Examples of gels are hydrogels, organogels and xerogels.

A cream is a semi-solid composition based on an emulsion of oil and water.

Examples of creams are oil-in-water (O/W) creams, which are composed of small droplets of oil dispersed in a continuous water phase, and water-in-oil (W/O) creams, which are composed of small droplets of water dispersed in a continuous oily phase.

In the present pharmaceutical composition sirolimus is used as compound a).

Sirolimus is a natural macrocyclic lactone produced by the bacterium *Streptomyces hygroscopicus*, with immunosuppressant properties. In cells, sirolimus binds to the immunophilin FK binding protein-12 (FKBP-12) to generate an immuno-suppressive complex that binds to and inhibits the activation of the mammalian Target Of Rapamycin (mTOR), a key regulatory kinase. This results in the inhibition of T lymphocyte activation and proliferation that occurs in response to antigenic and cytokine (IL-2, IL-4 and IL-15) stimulation and inhibition of antibody production. Further, sirolimus is an antibiotic antifungal drug.

The molecular formula of sirolimus is $C_{51}H_{79}NO_{13}$ and its IUPAC Name is (1R,9S,12S,15R,16E,18R,19R,21R,23S, 24E,26E,28E,30S,32S,35R)-1,18-dihydroxy-12-[(2R)-1-[(1S,3R,4R)-4-hydroxy-3-methoxycyclohexyl]propan-2-yl]-19,30-dimethoxy-15,17,21,23,29,35-hexamethyl-11,36-dioxa-4-azatricyclo[30.3.1.04,9]hexatriaconta-16,24,26,28-tetraene-2,3,10,14,20-pentone.

The structural formula of sirolimus is represented by Formula 1.

Formula 1

In line with the present invention sirolimus can also comprise enantiomers, hydrates, solvates and polymorphs thereof.

In an embodiment sirolimus is present in amorphous form.

In an alternative embodiment, sirolimus is present in crystalline form.

An amorphous form is a solid form having a short-range order but lacking a long-range order. On the other hand, a crystalline form is a solid form in which its constituents are arranged according to a long-range order in a crystal lattice that extends in all directions.

In an embodiment, the pharmaceutical composition comprises sirolimus as the only active agent.

In an alternative embodiment, the pharmaceutical composition comprises sirolimus and at least one further active agent.

In an embodiment, the content of sirolimus a) in the pharmaceutical composition is between 0.05 and 5.0 wt. %, preferably between 0.1 and 2.0 wt. %, more preferably between 0.2 and 1.0 wt. %, even more preferably between 0.25 and 0.75 wt. %, in particular about 0.4 wt. %, based on the total weight of the composition.

In another embodiment, the content of sirolimus a) in the pharmaceutical composition is about 0.05 wt. %, about 0.10 wt. %, about 0.15 wt. %, about 0.20 wt. %, about 0.25 wt. %, about 0.30 wt. %, about 0.35 wt. %, about 0.40 wt. %, about 0.45 wt. %, about 0.50 wt. %, about 0.55 wt. %, about 0.60 wt. %, about 0.65 wt. %, about 0.70 wt. %, about 0.75 wt. %, about 0.80 wt. %, about 0.85 wt. % about 0.90 wt. %, about 0.95 wt. % or 1.00 wt. %, based on the total weight of the composition.

Component b) of the pharmaceutical composition is a solvent. In line with this application a solvent is a substance being liquid at 23° C. and 101,325 kPa that dissolves a solute. In line with the application a solvent can comprise more than one solvent.

Examples of suitable solvents b) include, but are not limited to, water, dimethylsulfoxid (DMSO), alcohols such as ethanol, isopropanol, butanol, benzyl alcohol, ethylene glycol, propylene glycol, butanediols and isomers thereof, glycerin, amides such as N-methyl-2-pyrrolidone, dimethylacetamide and dimethylformamide (DMF), esters such as glycerin triacetate, diisopropyl adipate and ethyl oleate, cyclic ethers such as tetrahydrofuran (THF), dioxan and dimethyl isosorbide, and mixtures thereof.

In a preferred embodiment, solvent b) can be water, alcohol or mixtures thereof. It is preferred that the alcohol is an alcohol with 1 to 5 hydroxy groups, more preferably an alcohol with 2 or 3 hydroxy groups. In particular, solvent b) can comprise water, ethanol, propylene glycol, glycerin or mixtures thereof, especially solvent b) comprises a mixture of propylene glycol and glycerin.

In a preferred embodiment solvent b) does not comprise glycol ether d).

In an embodiment, the content of solvent b) in the pharmaceutical composition is between 75.0 and 98.5 wt. %, preferably between 85.0 and 98.0 wt. %, more preferably between 92.0 and 97.5 wt. %, especially between 94.5 and 96.5 wt. %, in particular about 95.6 wt. %, based on the total weight of the composition.

In another embodiment, the content of solvent b) in the pharmaceutical composition is about 75.0 wt. %, about 85.0 wt. %, about 90.0 wt. %, about 91.5 wt. %, about 92.5 wt. %, about 93.5 wt. %, about 94.5 wt. %, about 95.6 wt. %, about 96.5 wt. %, about 97.5 wt. % or about 98.5 wt. %, based on the total weight of the composition.

In another embodiment, solvent b) is a mixture of propylene glycol and glycerin in a ratio of between 20:1 and 1:2, more preferably between 10:1 and 2:1, especially between 7:1 and 3:1, in particular of about 5:1.

In another embodiment, solvent b) is a mixture of propylene glycol and glycerin in a ratio of about 10:1, about 9:1, about 8:1, about 7:1, about 6:1, about 5:1, about 4:1, about 3:1, about 2:1 or about 1:1.

Compound c) in the present pharmaceutical composition is a thickener.

A thickener c) is a substance which can increase the viscosity of a liquid without substantially changing its other properties. In line with the application a thickener can comprise more than one thickener.

Examples of suitable thickeners c) include, but are not limited to, alginic acid, bentonite, carbomer, carboxymethyl cellulose Ca, carboxymethyl cellulose Na, ethyl cellulose, gelatin, hydroxyethyl cellulose (HEC), hydroxyethylmethyl cellulose (HEMC), hydroxypropyl cellulose (HPC), glyceryl behenate, glyceryl monooleate, magnesium silicate, aluminium silicate, methyl cellulose, poloxamer, carbomer, polyethylene oxide, polyvinyl alcohol, povidone, propyleneglycol alginate, sodium alginate, polyacrylic acid, polyacrylamide, acrylamide/sodium acryloyldimethyl taurate copolymer, polyoxyethylene-(20)-sorbitan monolaurate (polysorbate 20), polyoxyethylene-(20)-sorbitan monopalmitate (polysorbate 40), polyoxyethylene-(20)-sorbitan monostearate (polysorbate 60) and polyoxy-ethylene-(20)-sorbitan monooleate (polysorbate 80) and mixtures thereof.

Preferably, in some embodiments, thickener c) includes ethyl cellulose, gelatin, hydroxyethyl cellulose (HEC), hydroxyethyl methyl cellulose (HEMC), hydroxypropyl cellulose (HPC), methyl cellulose, propylene glycol alginate, sodium alginate, polyacrylic acid, polyacrylamide, acrylamide/sodium acryloyldimethyl taurate copolymer, polyoxyethylene-(20)-sorbitan monolaurate (polysorbate 20), polyoxyethylene-(20)-sorbitan monopalmitate (polysorbate 40), polyoxyethylene-(20)-sorbitan monostearate (polysorbate 60), polyoxyethylene-(20)-sorbitan monooleate (polysorbate 80) and mixtures thereof.

In a preferred embodiment, thickener c) comprises acrylamide/sodium acryloyldimethyl taurate copolymer.

In an alternative preferred embodiment, thickener c) comprises polyoxyethylene-(20)-sorbitan monooleate (polysorbate 80).

In a particularly preferred embodiment, thickener c) comprises acrylamide/sodium acryloyldimethyl taurate copolymer and polyoxyethylene-(20)-sorbitan monooleate (polysorbate 80). Preferably, the ratio between the acrylamide/sodium acryloyldimethyl taurate copolymer and polyoxyethylene-(20)-sorbitan monooleate (polysorbate 80) is between 50:50 to 99:1, preferably between 75:25 to 98:2, more preferably between 85:15 to 97:3, even more preferably between 90:10 to 95:5.

The content of thickener c) in the pharmaceutical composition is between 0.05 and 10.0 wt. %, preferably between 1.0 and 5.0 wt. %, more preferably between 1.5 and 4.5 wt. %, especially between 2.0 and 4.0 wt. %, in particular about 3.0 wt. %, based on the total weight of the composition.

In another embodiment, the content of thickener c) in the pharmaceutical composition is about 0.5 wt. %, about 1.0 wt. %, about 1.5 wt. %, about 2.0 wt. %, about 2.5 wt. %, about 3.0 wt. %, 3.5 wt. %, 4.0 wt. %, 4.5 wt. %, 5.0 wt. % or 5.5 wt. %, based on the total weight of the composition.

Compound d) in the present pharmaceutical composition is glycol ether. In line with the application a glycol ether can comprise more than one glycol ether.

Examples of suitable glycol ethers d) include, but are not limited to, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, propylene glycol methyl ether, diethylene glycol monomethyl ether, diethylene glycol monoethyl ether, diethylene glycol mono-n-butyl ether, dipropyleneglycol methyl ether, ethylene glycol dimethyl ether, ethylene glycol diethyl ether, ethylene glycol dibutyl ether, ethylene glycol methyl ether acetate, ethylene glycol monoethyl ether acetate, ethylene glycol monobutyl ether acetate, propylene glycol methyl ether acetate and mixtures thereof.

Preferably, glycol ether d) includes ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monoethyl ether, diethylene glycol mono-n-butyl ether and mixtures thereof.

In a particular embodiment, glycol ether d) is diethylene glycol monoethyl ether.

The content of glycol ether d) in the pharmaceutical composition is between 0.05 and 10.0 wt. %, preferably between 0.5 and 5.0 wt. %, more preferably between 1.5 and 4.5 wt. %, especially between 2.0 and 4.0 wt. %, in particular about 3.0 wt. %, based on the total weight of the composition.

In another embodiment, the content of glycol ether d) in the pharmaceutical composition is about 0.5 wt. %, about 1.0 wt. %, about 1.5 wt. %, about 2.0 wt. %, about 2.5 wt. %, about 3.0 wt. %, about 3.5 wt. %, about 4.0 wt. %, about 4.5 wt. %, about 5.0 wt. %, or about 5.5 wt. %, based on the total weight of the composition.

In an embodiment, the pharmaceutical composition may further comprise antioxidant e).

Antioxidants are substances that inhibit oxidation of the other compounds in the composition and so prevent their degradation and thus increase stability of the composition.

Examples of suitable antioxidants e) include, but not limited to, ascorbic acid, ascorbyl palmitate, hypophosphorous acid, vitamin E and its derivatives, α-tocopherol, ψ-tocopherol, δ-tocopherol, octyl gallate, dodecyl gallate, butylated hydroxy anisole (BHA), butylated hydroxy toluene (BHT), D-α-tocopheryl polyethylene glycol 1000 succinate, potassium metabisulfite, sodium bisulfite, sodium formaldehyde sulfoxylate, sodium metabisulfite, sodium sulfite, sodium thiosulfate, sulfur dioxide, propyl gallate (PG) and mixtures thereof.

In a preferred embodiment, antioxidant e) includes derivates of ascorbic acid, such as ascorbic acid and ascorbyl palmitate and derivates of gallic acid, for example octyl gallate, dodecyl gallate, propyl gallate (PG) and mixtures thereof. Even more preferably, antioxidant e) includes derivates of gallic acid.

Especially, antioxidant e) includes octyl gallate, dodecyl gallate, propyl gallate (PG) and mixtures thereof. In particular, antioxidant e) is propyl gallate (PG).

In an embodiment, the content of antioxidant e) in the pharmaceutical composition is between 0.01 and 0.50 wt. %, preferably between 0.01 and 0.20 wt. %, more preferably between 0.02 and 0.10 wt. %, especially between 0.03 and 0.07 wt. %, in particular about 0.04 wt. %, based on the total weight of the composition.

In another embodiment, the content of antioxidant e) in the pharmaceutical composition is about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, or about 0.10 wt. %, based on the total weight of the composition.

In another embodiment, the pharmaceutical composition is stable for 4 weeks at a temperature of about 25° C. and a humidity of about 60% RH. Alternatively preferably, the pharmaceutical composition is stable for 12 weeks at a temperature of about 25° C. and a humidity of about 60% RH. Alternatively preferably, the pharmaceutical composition is stable for 6 months at a temperature of about 25° C. and a humidity of about 60% RH. Alternatively preferably, the pharmaceutical composition is stable for 9 months at a temperature of about 25° C. and a humidity of about 60% RH. Alternatively preferably, the pharmaceutical composition is stable for 1 year at a temperature of about 25° C. and a humidity of about 60% RH.

Alternatively preferably, the pharmaceutical composition is stable for 6 months when stored at a temperature of 2° C. to 8° C. Alternatively preferably, the pharmaceutical composition is stable for 1 year when stored at a temperature of 2° C. to 8° C. Alternatively preferably, the pharmaceutical composition is stable for 18 months when stored at a temperature of 2° C. to 8° C. Alternatively preferably, the pharmaceutical composition is stable for 3 years when stored at a temperature of 2° C. to 8° C. Storage at 2° C. to 8° C. can for example be carried out in a refrigerator.

The pharmaceutical composition is stable if the content of undegraded sirolimus is higher than 90.0% w/w, preferably higher than 92.0% w/w, more preferably higher than 93.5% w/w, even more preferably higher than 95.0% w/w, even more preferably higher than 97% w/w, even more preferably higher than 99.0% w/w of the whole amount of sirolimus. Otherwise said, the pharmaceutical composition is stable if the content of degradational products of sirolimus is less than or equal to 10% w/w, preferably less than or equal to 8% w/w, more preferably less than or equal to 6.5% w/w, even more preferably less than or equal to 5% w/w, even more preferably less than or equal to 3% w/w, even more preferably less than or equal to 1% w/w of the whole amount of sirolimus. The content of sirolimus is measured with Analytical method 1 as described in the experimental section.

Moreover, the permeability and distribution of sirolimus in skin layers are intrinsically linked to viscous properties of a pharmaceutical composition. Hence, viscosity is a critical quality of the pharmaceutical composition for the indication of permeability properties of sirolimus in the composition.

In an embodiment, the pharmaceutical composition has a viscosity between 1 mPas and 250 000 mPas, preferably between 10 000 mPas and 150 000 mPas, more preferably between 20 000 mPas and 120 000 mPas, even more preferably between 30 000 mPas and 90 000 mPas, even more preferably between 40 000 mPas and 80 000 mPas, especially between 60 000 mPas and 75 000 mPas, in particular 70 000 mPas.

The viscosity and torque of the pharmaceutical composition can be measured as described in the experimental section.

In a preferred embodiment the composition comprises:
a) between 0.05 and 5.0 wt. %, preferably between 0.1 and 2.0 wt. %, especially between 0.25 and 0.75 wt. %, in particular about 0.4 wt. % of sirolimus, based on the total weight of the composition,
b) between 75.0 and 98.5 wt. %, more preferably between 92.0 and 97.5 wt. %, especially between 94.5 and 96.5 wt. %, in particular about 95.6 wt. % of solvent b), based on the total weight of the composition,
c) between 0.05 and 10.0 wt. %, preferably between 1.0 and 5.0 wt. %, especially between 2.0 and 4.0 wt. %, in particular about 3.0 wt. % of thickener c), based on the total weight of the composition; and
d) between 0.05 and 10.0 wt. %, preferably between 1.5 and 4.5 wt. %, especially between 2.0 and 4.0 wt. %, in particular about 3.0 wt. % of glycol ether d), based on the total weight of the composition.

In a preferred embodiment the composition comprises:
a) between 0.05 and 5.0 wt. %, preferably between 0.1 and 2.0 wt. %, especially between 0.25 and 0.75 wt. %, in particular about 0.4 wt. % of sirolimus, based on the total weight of the composition,
b) between 75.0 and 98.0 wt. %, more preferably between 92.0 and 97.5 wt. %, especially between 94.5 and 96.5 wt. %, in particular about 95.6 wt. % of solvent b), based on the total weight of the composition,
c) between 0.05 and 10.0 wt. %, preferably between 1.0 and 5.0 wt. %, especially between 2.0 and 4.0 wt. %, in particular about 3.0 wt. % of thickener c), based on the total weight of the composition,
d) between 0.05 and 10.0 wt. %, preferably between 1.5 and 4.5 wt. %, especially between 2.0 and 4.0 wt. %, in particular about 3.0 wt. % of glycol ether d), based on the total weight of the composition, and
e) between 0.01 and 0.50 wt. %, preferably between 0.02 and 0.10 wt. %, especially between 0.03 and 0.07 wt. %, in particular about 0.04 wt. % of antioxidant e), based on the total weight of the composition.

In a more preferred embodiment the composition comprises:
a) between 0.05 and 5.0 wt. %, preferably between 0.1 and 2.0 wt. %, especially between 0.25 and 0.75 wt. %, in particular about 0.4 wt. % of sirolimus, based on the total weight of the composition,
b) between 75.0 and 98.5 wt. %, more preferably between 92.0 and 97.5 wt. %, especially between 94.5 and 96.5 wt. %, in particular about 95.6 wt. % of solvent b), based on the total weight of the composition,
c) between 0.05 and 10.0 wt. %, preferably between 1.0 and 5.0 wt. %, especially between 2.0 and 4.0 wt. %, in particular about 3.0 wt. % of thickener c), based on the total weight of the composition, and
d) between 0.05 and 10.0 wt. %, preferably between 1.5 and 4.5 wt. %, especially between 2.0 and 4.0 wt. %, in particular about 3.0 wt. % of glycol ether d), based on the total weight of the composition,
wherein solvent b) is a mixture of propylene glycol and glycerin, preferably in a ratio of between 7:1 and 3:1, in particular of about 5:1, wherein thickener c) is a mixture of acrylamide/sodium acryloyldimethyl taurate copolymer and polyoxyethylene-(20)-sorbitan monooleate (polysorbate 80) preferably in a ratio of between 85:15 to 97:3, in particular in a ratio between 90:10 to 95:5, and wherein glycol ether d) is diethylene glycol monoethyl ether.

In an even more preferred embodiment the composition comprises:
a) between 0.05 and 5.0 wt. %, preferably between 0.1 and 2.0 wt. %, especially between 0.25 and 0.75 wt. %, in particular about 0.4 wt. % of sirolimus, based on the total weight of the composition,
b) between 75.0 and 98.0 wt. %, more preferably between 92.0 and 97.5 wt. %, especially between 94.5 and 96.5 wt. %, in particular about 95.6 wt. % of solvent b), based on the total weight of the composition,
c) between 0.05 and 10.0 wt. %, preferably between 1.0 and 5.0 wt. %, especially between 2.0 and 4.0 wt. %, in particular about 3.0 wt. % of thickener c), based on the total weight of the composition
d) between 0.05 and 10.0 wt. %, preferably between 1.5 and 4.5 wt. %, especially between 2.0 and 4.0 wt. %, in particular about 3.0 wt. % of glycol ether d), based on the total weight of the composition, and
e) between 0.01 and 0.50 wt. %, preferably between 0.02 and 0.10 wt. %, especially between 0.02 and 0.07 wt. %, in particular about 0.04 wt. % of antioxidant e), based on the total weight of the composition, wherein solvent b) is a mixture of propylene glycol and glycerin in the ratio of between 7:1 and 3:1, in particular of about 5:1, wherein thickener c) is a mixture of acrylamide/sodium acryloyldimethyl taurate copolymer and polyoxy-ethylene-(20)-sorbitanmonooleate (polysorbate 80) preferably in a ratio of between 85:15 to 97:3, in particular in a ratio between 90:10 to 95:5, wherein glycol ether d) is diethylene glycol monoethyl ether, and wherein the antioxidant e) is propyl gallate.

Another subject of the invention is the present composition for use in the treatment of skin diseases and/or skin manifestations of diseases.

In an embodiment, the skin diseases or skin manifestations of diseases include genodermatoses, skin manifestations resulting from vascular conditions, malignant and benign skin tumors, skin manifestations of auto-immune/inflammatory conditions, skin manifestations of infection and infestation, other miscellaneous skin conditions, and/or skin manifestations of tuberous sclerosis complex (TSC).

Genodermatosis is a hereditary skin disease with three inherited modes including single gene inheritance, multiple gene inheritance and chromosome inheritance. Genodermatosis includes neurofibromatosis type I, Muir-Torre syndrome, Proteus syndrome, Brooke-Speigler syndrome, hamartomatous polyposis syndromes such as Peutz-Jeghers syndrome, juvenile polyposis syndrome and PTEN hamartomatous tumor syndromes comprising for example Cowden's disease Proteus-like Syndrome and Bannayan-Riley-Ruvalcaba syndrome, pachyonychia congenita, familial multiple discoid fibromas, Birt-Hogg-Dubé syndrome including fibrofolliculomas, multiple familial trichoepitheliomas, hyperkeratosis lenticularis perstans, focal acral hyperkeratosis, lichenoid keratosis, Conradi-Eltinermann, epidermolytic ichthyosis, erythrokeratoderma variabilis, ichthyosis hystrix, KID syndrome, Netherton syndrome, Olmsted syndrome, Refsum disease, Sjogren-Larsson Syndrome, Hailey-Hailey disease, overgrowth syndromes, xeroderma pigmentosum, epidermolytic palmoplantar keratoderma, and/or epidermolysis bullosa simplex.

The skin manifestations resulting from vascular conditions may include port-wine stains such as Sturge-Weber syndrome, blue rubber bleb nevus syndrome, infantile hemangioma such as PHACE syndrome, kaposiform hemangio endothelioma such as Kasabach-Merritt phenomenon, cutaneous lymphatic malformation, cystic lymphangioma, cavernous lymphangioma, diffuse microcystic lymphatic malformations, venous malformation, hemangioma, refractory hemangioendotheliomas in Maffucci syndrome essential telangiectasias, cherry angiomas and/or vascular anomalies such as complicated vascular anomalies.

The malignant and benign skin tumors comprise basal cell nevus syndrome, Kaposi's sarcoma, cutaneous T-cell lymphomas, cutaneous Castleman Disease, dermatofibrosarcoma protruberans, extramammary Paget, basal cell carcinoma, squamous cell carcinoma, melanoma, merkel cell carcinoma, extramammary Paget, actinic keratosis, keratosis pilaris, epidermal nevi, follicular hyperkeratosis, lentigines, nevus Araneus, seborrheic keratosis, nevus sebaceous, and/or epidermal nevus.

The skin manifestations of auto-immune/inflammatory conditions include, chronic plaque psoriasis, lichen planus, lichen sclerosus, erosive oral and plantar lichen planus, systemic sclerosis, cutaneous acute graft-versus-host disease, cutaneous chronic graft-versus-host disease, oral graft-versus-host disease, sclerodermatous graft-versus-host disease, contact dermatitis, drug-induced dermatitis, allergic dermatitis, dyshydrotic eczema, erythema multiforme, hives, panniculitis, pemphigoid, pemphigus, vitiligo, cutaneous sarcoidosis, lupus, pyogenic granulomas, cheilitis granulomatosis and confluent and/or reticulated papillomatosis.

Skin manifestations of infection and infestation include acne, carbunculosis, cellulitis, furunculosis, ecthyma, erysipela, impetigo, bacterial vaginosis, athlete's foot, dermatophytosis, candidiasis, onychomycosis, tinea alba, tinea pedis, tinea unguium, tinea manuum, tinea cruris, tinea corporis, tinea capitis, tinea faciei, tinea barbae, tinea imbricata, tinea nigra, tinea versicolor, tinea incognito, balanitis, vaginal yeast infection, paronychia, warts, genital warts, herpes, milker's nodules, molluscum contagiosum, trichomoniasis, filariasis, cutaneous larva migrans, insect bites, myiasis, scabies, furuncular myiasis, migratory myiasis and/or pediculosis.

Skin manifestations of miscellaneous causes include pityriasis, keloid, plantar hyperkeratosis, multiple minute digitate hyperkeratosis, stasis dermatitis, hyperhidrosis, calluses, nummular dermatitis, perioral dermatitis, neurodermatitis, seborrheic dermatitis, granuloma, acanthosis nigricans, bromhidrosis, decubitus ulcer, hyperhidrosis, miliaria, pruritis vulvae, rosacea, and/or gingival hypertrophy.

Tuberous sclerosis complex (TSC) is an autosomal dominant genetic disease that causes non-cancerous tumors as described above.

Preferably, the present pharmaceutical composition is used for the treatment of skin manifestations of tuberous sclerosis complex (TSC).

Further preferably, the skin manifestations of tuberous sclerosis complex (TSC) may include hypomelanic macules, facial angiofibromas, ungual fibromas also known as Koenen's tumors, fibrous cephalic plaques, shagreen patches, intraoral fibromas and combinations thereof.

Hypomelanic macules are present in about 90% of people with TSC. These small white or lighter patches of skin may appear anywhere on the body and are caused by a lack of melanin.

Facial angiofibromas are present in about 75% of people with TSC. These are a rash of reddish spots or bumps on the nose and cheeks in a butterfly distribution which consist of blood vessels and fibrous tissue.

Further, ungual fibromas, also known as Koenen's tumors, are small fleshy tumors that grow around and under the toenails or fingernails. These are rare in people with TSC in childhood but common by middle age. They are generally more common on toes than on fingers and usually develop at around 15-29 years of age.

Next, fibrous cephalic plaques are present in about 25% of people with TSC. These are raised, discolored areas usually found on the forehead, but sometimes on the face or elsewhere on the scalp.

Also, shagreen patches are present in about half of people with TSC, appearing in childhood. They are areas of thick leathery skin that are dimpled like an orange peel and pigmented. They are usually found on the lower back or nape or scattered across the trunk or thighs. The frequency of these lesions rises with age.

Intraoral fibromas are small-surface tumours found in the gums, inside the cheeks or on the tongue. Gum (gingival) fibromas are found in about 20-50% of people with TSC, more commonly in adults.

Most preferably, the present pharmaceutical composition is used for the treatment of facial angiofibromas.

In an embodiment, the skin diseases and skin manifestations of diseases listed hereinabove are treated with the present pharmaceutical composition by applying the pharmaceutical composition twice daily, once daily, every second day and/or once weekly.

The method of the present invention for producing the pharmaceutical composition of the present invention comprises the steps of (i) providing sirolimus a), and (ii) forming the present composition.

In a preferred embodiment, step (i) comprises the identification and/or the determination of the purity of sirolimus a). Further step (i) preferably comprises weighing the corresponding quantity of sirolimus a).

In step ii) the present composition is formed. As far as the components comprised in the composition and the contents of these components are concerned, the same as described above applies.

In an embodiment, step ii) comprises:

a sub step iia) of forming a solution of sirolimus a) in solvent b) and glycol ether d) and a sub step iib) of adding thickener c) to the solution of sub step iia).

In an embodiment, sub step iia) comprises dissolving sirolimus a) in glycol ether d), mixing the resulting mixture with solvent b) and homogenizing the final mixture.

Homogenizing can comprise mechanical treatment of the mixture such as stirring and/or ultrasonic treatment, preferably stirring. Preferably, the resulting mixture is homogenized until dissolution, preferably complete dissolution, of sirolimus a).

Complete dissolution of sirolimus a) results in a solution which can be confirmed by visual inspection. Preferably, stirring can be performed manually or automatically with a stirring speed between 1 and 10 000 rpm, preferably between 30 and 1 000 rpm, and the stirring time between 0.5 and 360 min, preferably between 10 and 60 min, in particular 25 min. Preferably, ultrasonic treatment can be performed with industrially available ultrasonic devices, such as UP400St and UIP4000hdT, preferably with a sound frequency between 18 kHz and 30 kHz, more preferably between 18 kHz and 20 kHz and with a power between 50 W and 16 kW, preferably between 1.5 kW and 10.0 kW.

In a preferred embodiment, homogenizing can be carried out at a temperature of between 8° C. and 35° C., preferably of between 15° C. and 30° C., more preferably of between 23° C. and 27° C., in particular at about 25° C.

In an alternative embodiment, sub step iia) comprises dissolving sirolimus a) in solvent b), further mixing the resulting mixture with glycol ether d) and homogenizing the final mixture. Homogenizing is defined as described hereinabove.

In another embodiment, sub step iia) comprises preparing a homogenous mixture of solvent b) and glycol ether d), dissolving sirolimus a) in the resulting mixture and homogenizing the final mixture. Homogenizing is defined as described hereinabove.

Furthermore, sub step iib) comprises adding thickener c) to the mixture of sirolimus a), solvent b) and glycol ether d) and homogenizing the resulting mixture as described hereinabove, preferably by stirring. Preferably, the stirring is continued until a clear homogenous gel is formed.

In another embodiment, step ii) comprises adding antioxidant e) to the solution according to sub step iia) as described above. Preferably, antioxidant e) can be added at any stage during the formation of the solution according to sub step iia).

EXPERIMENTAL SECTION

1. Analytical Methods 1.1 HPLC (Analytical Method 1)

A sample solution having a concentration of about 100 µg/mL and a standard solution having a concentration of 100 µg/mL were prepared, optionally filtered through a 0.45 m nylon syringe filter and subsequently subjected to a high-pressure liquid chromatography (HPLC) method using the parameters in Table 1:

TABLE 1

| Parameters. | |
| --- | --- |
| Instrument | HPLC-Waters Alliance 2695 |
| Chromatographic Mode | Gradient |
| Diluent | 100% acetonitrile |
| Mobile phase | Gradient elution program (c.f. Table 2) |
| Column | X-Bridge C18, 150 mm × 4.6 mm, 3.5 µm |
| Wavelength | 277 nm |
| Flow rate | Gradient |
| Injection volume | 10 µL |
| Syringe draw rate | Fast |
| Sampling rate | 20 points/sec |
| Column oven temperature | 60° C. |
| Sample cooler temperature | 15° C. |
| Run time | 20 minutes |
| Needle wash fluid | Acetonitrile: water (95:5) |
| Seal wash fluid | Acetonitrile: water (20:80) |

The elution occurred according to the gradient elution program as shown in Table 2.

TABLE 2

| Gradient elution program | | | |
| --- | --- | --- | --- |
| Time (min) | Flow rate (mL/min) | Share of Mobile phase-A: 100% Milli-Q-water (%) in the mobile phase | Share of Mobile phase-B: 100% acetonitrile (%) in the mobile phase |
| --- | --- | --- | --- |
| 0.0 | 1.0 | 45 | 55 |
| 5.0 | 2.0 | 45 | 55 |
| 15.0 | 2.0 | 40 | 60 |
| 17.0 | 1.0 | 10 | 90 |
| 18.1 | 1.0 | 45 | 55 |
| 20.0 | 1.0 | 45 | 55 |

In addition, before evaluating chromatograms the corresponding criteria of the following parameters had to be fulfilled:

TABLE 3

| Evaluation parameters | | |
| --- | --- | --- |
| Step | Parameters | Criteria |
| --- | --- | --- |
| 1. | Theoretical plates for sirolimus peaks in standard chromatogram. | NLT 2000 |
| 2. | Tailing for sirolimus peaks in standard chromatogram. | NMT 2.0 |
| 3. | % RSD for sirolimus peaks areas of replicate standard injections. | NMT 2.0% |
| 4. | % RSD for sirolimus peak areas of replicate standard injection and bracketing standard injections | NMT 2.0% |

Calculation/Assay

Taking the HPLC chromatogram into account the assay of sirolimus in sample solution was calculated by the following equation:

Equation for calculation of sirolimus assay in a sample according to

Analytical method 1

$$\% \text{ Assay} = \frac{AS_{sp1}}{AS_{std}} \times \frac{W_{std}}{25} \times \frac{5}{20} \times \frac{50}{W_{sp1}} \times \frac{AW}{LC} \times P \qquad \text{Equation 1}$$

wherein $AS_{spl}$ is the sum of areas of isomer B and isomer C of sirolimus in the chromatogram of the sample solution, $AS_{std}$ is the average of sum of areas of isomer B and isomer C in chromatograms of the standard solution, $W_{std}$ is the weight of sirolimus standard in mg, $W_{spl}$ is the weight of the sample in mg, P is the purity of sirolimus standard in %, AW is the average sample weight and LC is the labelled claim of sirolimus in the sample, such that the ratio LC/AW represents a labelled/expected concentration of sirolimus in the sample.

FIG. 1 and FIG. 2 show examples of chromatograms of the standard solution and the sample solution obtained with the above-described analytical method. Both chromatograms comprise two main peaks corresponding to isomer B and isomer C of sirolimus. Isomer B of sirolimus contains an intramolecular hemiketal, forming a six-membered ring, wherein isomer C of sirolimus also contains intramolecular hemiketal but including a neighbouring keto group, and thus forming a seven-membered ring (oxepane). Further, there exists an isomer A believed to be the transient intermediate, lacking hemiketal. Thereby, the retention time of isomer B was around 10.0-10.1 min and the retention time of isomer C was around 11.0-11.1 min. The sum of areas under the curve of these two peaks was used for determination of the assay of sirolimus in the sample. Thereby, an average sum of areas of isomer B and isomer C in chromatograms of the standard solution was compared to the sum of areas of isomer B and isomer C in the chromatogram of the sample solution.

1.2 HPLC (Analytical Method 2)

Table 4 represents parameters of the Analytical method 2 being a reverse phase HPLC method for assay determination of sirolimus in a sample. Other steps and parameters of the method such as the preparation of the sample and standard solutions, chromatogram evaluation and assay determination of sirolimus in the sample solution correspond to Analytical method 1.

TABLE 4

HPLC method parameters for detection of sirolimus in IVRT and IVPT
HPLC method parameter

| HPLC method type | Reverse phase |
|---|---|
| Detection | Shimadzu UV-VIS Detector |
| Column | Shimadzu C18 |
| Wavelength | 277 nm |
| Method mode | Isocratic |
| Mobile phase | Mobile phase A: 20% water |
| | Mobile phase B: 80% acetonitrile |
| Flow rate | 1.5 mL/min |
| Injection volume | 10 µL |
| Retention time | Around 4.3 min |

2. Viscosity Method

Samples in the range of 500-600 mg were measured according to the cone plate method with a Brookfield RV or Brookfield DV-II+ pro viscosimeter connected to a Rheocalc 32 software. The measurements were performed with spindles CP-51 (cone angle 1.565°) or CP-52Z (cone angle 3.0°). Using the CP-52Z spindle, viscosity measurements were performed at the rotation speed of 1.0 rpm. On the other hand, using the CP-51 spindle, viscosity measurements were performed at the rotation speed of 0.50 rpm.

Measurements were performed according to the BEVIS program of the Brookfield RV viscometer with the program details provided in Table 5, wherein WTI stands for "wait for time interval", SSN for "set viscometer speed" and DCI for "data collection interval".

TABLE 5

Program details of BEVIS program for subsequent viscosity measurements

| Brookfield Engineering Viscometer Instruction Set (BEVIS Commands) | Value (min) |
|---|---|
| WTI | 00:01:00 |
| SSN | 00:01:00 |
| DCI | 01:00 |
| WTI | 00:15:00 |

3. Release and Permeability Studies 3.1 In Vitro Release Test (IVRT)

The IVRT study was performed according to the parameters presented in Table 6.

TABLE 6

IVRT parameters

| API | Sirolimus |
|---|---|
| Release membrane | Polyether sulfone (PES) membrane |
| Membrane pore size | 0.45 µm |
| Dose of pharmaceutical composition | 250 mg |
| Active diffusion area of cell | 0.60 cm² |
| Number of Franz cells | 18 |
| Volume of Franz cells | 4.8 mL |
| Receptor fluid | EtOH/water (85: 15) |
| Sample collection | 300 µL |
| Sample storage condition | Refrigerator (2-8° C.) |
| Time points | 0.5 h, 1 h, 2 h, 3 h, 4 h, 5 h, 6 h |

Before filling into the receptor chamber of a Franz diffusion cell, the receptor fluid was degassed through a sampling tube using a transfer pipette. Further, a magnetic stir bar was placed into the receptor chamber of the Franz diffusion cell. During the experiment, the receptor fluid was regularly checked for the presence of air bubbles on the downside of the membrane, whereby the Franz diffusion cell was tilted such that the air bubbles could move through the sampling port to the outside. Moreover, the Franz diffusion cell was placed into a jacket surrounding the receptor chamber of the Franz diffusion cell with a constant temperature of 32° C. At each time point 300 µL of release fluid was withdrawn from the receptor chamber and replaced with 300 µL of fresh receptor fluid. The withdrawn samples were analyzed for the content of sirolimus by HPLC with Analytical method 2 (c.f. item 1.2).

3.2 In Vitro Permeability Test (IVPT)

The IVPT was performed according to the parameters presented in Table 7.

TABLE 7

IVPT parameters

| API | Sirolimus |
|---|---|
| Type of membrane | Human cadaver skin |

TABLE 7-continued

| IVPT parameters | |
| --- | --- |
| Study length | 24 h |
| Dose of pharmaceutical composition | 10 mg |
| Volume of Franz diffusion cells | 4.8 mL |
| Active diffusion area | 0.64 cm$^2$ |
| Receptor fluid | Phosphate buffered saline (PBS) + 0.01% gentamicin + 2% BrijO20 |
| Sampling time points | 0 h, 4 h, 8 h ,12 h, 24 h |
| Volume of each collected sample | 300 μL |
| Storage of collected samples | Refrigerator (2-8° C.) |
| Skin washing | IPA: water (80:20) |
| Epidermis & dermis separation | Yes |
| Extraction solvent | 3 mL of 80:20 methanol-water mixture |
| Extraction conditions | 24 h at room temperature with regular turning around |
| Extraction sample volume | 500 μL |

The IVPT was performed using a standard Franz diffusion cell having human cadaver skin serving as a release membrane. Before the experiment, the human cadaver skin was taken out of a freezer (where it had been stored at about –20° C.) and was let to thaw at room temperature for 15 min. Afterwards the skin was submerged in phosphate buffered saline (PBS) for an additional 15 min for complete hydration of the skin. Subsequently the skin was cut into pieces of about 2.0 cm$^2$. A skin piece was gently wiped with lint free wipes and thereafter sandwiched between donor chamber and receptor chamber of the Franz diffusion cell.

The receptor fluid was degassed before being filled into the receptor chamber through a sampling tube. The receptor fluid was regularly checked for the presence of air bubbles on the downside of the skin membrane, wherein the Franz diffusion cell was tilted if air bubbles were noticed such that the air bubbles could move through the sampling port to the outside. Also, the receptor fluid was stirred with a magnetic stir bar provided in the receptor chamber. Moreover, the Franz diffusion cell was placed into a jacket surrounding the receptor chamber of the Franz diffusion cell at a constant temperature of 32° C. A skin impedance test was performed to check the integrity of the skin before starting the experiment.

At each time point 300 μL of release fluid was withdrawn from the receptor chamber and replaced with 300 μL of fresh receptor fluid. The withdrawn samples were analyzed for the content of sirolimus with Analytical method 2 (c.f. item 1.2).

Additionally, after the last sampling of the receptor fluid the skin piece was removed from the Franz diffusion cell and washed with a mixture of isopropyl alcohol (ISA) and water in a ratio 80:20. The cleaned skin pieces were tape stripped three times, thereby separating epidermis from the dermis. Next, sirolimus retained in the epidermis (on the tapes) and in the dermis (remains of the skin pieces) was extracted from the epidermis and dermis with the extraction solvent. To do so, the tapes and the remains of the skin pieces were separately immersed into 3 mL of the extraction solvent for 24 h at room temperature. Afterwards the extraction solvent was analyzed for the content of sirolimus by HPLC with Analytical method 2 (c.f. item 1.2).

Example 1—Gel Preparation 0.04 g of propyl gallate were dissolved in 3.00 g of diethylene glycol monoethyl ether under stirring. Subsequently, 0.40 g of sirolimus were dissolved in the mixture of propyl gallate and diethylene glycol monoethyl ether under stirring. In parallel, 15.00 g of glycerin and 78.56 g of propylene glycol were mixed under stirring. In the next step, the mixture of sirolimus, propyl gallate and diethylene glycol monoethyl ether was added to the mixture of glycerin and propylene glycol under stirring. Further, 3.00 g of acrylamide/sodium acryloyldimethyl taurate copomolymer/polyoxyethylene-(20)-sorbitan monooleate were added under stirring to the mixture of sirolimus, propyl gallate, diethylene glycol monoethyl ether, glycerin and propylene glycol. Afterwards, the mixture was stirred until a clear homogenous transparent gel was formed containing the substances of Table 8.

TABLE 8

| | | Qty/batch (g) Batch size (100 g) | wt. % com- posi- tion |
| --- | --- | --- | --- |
| Sr. No. | Ingredients | | |
| a) | Sirolimus | 0.40 | 0.40 |
| b) | Glycerin | 15.00 | 15.00 |
| | Propylene glycol | 78.56 | 78.56 |
| c) | Acrylamide/sodium acryloyldimethyl taurate copomolymer/& polyoxyethylene-(20)-sorbitanmonooleate (Sepineo P 600 ®) in ratio of about 95:5 | 3.00 | 3.00 |
| d) | Diethylene glycol monoethyl ether (Transcutol P®) | 3.00 | 3.00 |
| e) | Propyl gallate | 0.04 | 0.04 |
| | Total weight (g) | 100.00 | 100.00 |

Content of the pharmaceutical composition of Example 1

Example 2—Gel Preparation 0.04 g of propyl gallate were dissolved in 3.00 g of diethylene glycol monoethyl ether under stirring. Subsequently, 0.40 g of sirolimus were dissolved in the mixture of propyl gallate and diethylene glycol monoethyl ether under stirring. In parallel, 5.00 g of ethanol and 88.56 g of purified water were mixed under stirring. In the next step, the mixture of sirolimus, propyl gallate and diethylene glycol monoethyl ether was added to the mixture of ethanol and purified water under stirring. Further, 3.00 g of acrylamide/sodium acryloyldimethyl taurate copomolymer/polyoxyethylen-(20)-sorbitan monooleat were added under stirring to the mixture of sirolimus, propyl gallate, diethylene glycol monoethyl ether ethanol and purified water. Afterwards, the mixture was stirred until a clear homogenous gel was formed containing the substances of Table 9.

TABLE 9

| | | Qty/batch (g) Batch size (100 g) | wt. % com- posi- tion |
| --- | --- | --- | --- |
| Sr. No. | Ingredients | | |
| a) | Sirolimus | 0.40 | 0.40 |
| b) | Ethanol | 5.00 | 5.00 |
| | Purified Water | 88.56 | 88.56 |
| c) | Acrylamide/ sodium acryloyldimethyl taurate copolymer/ polyoxyethylen-(20)-sorbitan monooleat (Sepineo P 600) in ratio of about 95:5 | 3.00 | 3.00 |

Composition of pharmaceutical composition of Example 2.

TABLE 9-continued

Composition of pharmaceutical composition of Example 2.

| Sr. No. | Ingredients | Qty/batch (g) Batch size (100 g) | wt. % com-posi-tion |
|---------|-------------|------|------|
| d) | Diethylene glycol monoethyl ether (Transcutol P ®) | 3.00 | 3.00 |
| e) | Propyl gallate | 0.04 | 0.04 |
| | Total weight (g) | 100.00 | 100.00 |

Example 3—Viscosity Experiment

The pharmaceutical compositions of Example 1 and Example 2 were tested for their viscosity properties. Each viscosity was measured with the above-described method using a spindle CP-52Z at the rotation speed of 1 rpm.

Tables 10 and 11 show the viscosity data for each subsequent measurement of viscosity of three triplicates of the pharmaceutical composition of Example 1 and of one replicate of the pharmaceutical composition of Example 2, respectively.

TABLE 10

Viscosity and torque measurements of the pharmaceutical composition of Example 1 with spindle CP-52Z at a rotation speed of 1 rpm

| Sr. No. | First measurement Viscosity (mPas) | Torque (%) | Second measurement Viscosity (m Pas) | Torque (%) | Third measurement Viscosity (mPas) | Torque (%) |
|---------|-----------|------|-----------|------|-----------|------|
| 1 | 70247.76 | 70.8 | 64096.12 | 64.6 | 69553.22 | 70.1 |
| 2 | 71934.50 | 72.5 | 67072.72 | 67.6 | 69950.10 | 70.5 |
| 3 | 72132.94 | 72.7 | 67965.70 | 68.5 | 70049.32 | 70.6 |
| 4 | 72132.94 | 72.7 | 68362.58 | 68.9 | 70346.98 | 70.9 |
| 5 | 72331.38 | 72.9 | 68660.24 | 69.2 | 70148.54 | 70.7 |
| 6 | 72232.16 | 72.8 | 68858.68 | 69.4 | 70148.54 | 70.7 |
| 7 | 72132.94 | 72.7 | 68858.68 | 69.4 | 70247.76 | 70.8 |
| 8 | 72232.16 | 72.8 | 68858.68 | 69.4 | 70247.76 | 70.8 |
| 9 | 72132.94 | 72.7 | 68957.90 | 69.5 | 70148.54 | 70.7 |
| 10 | 72033.72 | 72.6 | 69057.12 | 69.6 | 70148.54 | 70.7 |
| 11 | 71934.50 | 72.5 | 69057.12 | 69.6 | 70148.54 | 70.7 |
| 12 | 71736.06 | 72.3 | 69057.12 | 69.6 | 70148.54 | 70.7 |
| 13 | 71438.40 | 72.0 | 69057.12 | 69.6 | 70148.54 | 70.7 |
| 14 | 71140.74 | 71.7 | 69057.12 | 69.6 | 70148.54 | 70.7 |

TABLE 11

Viscosity and torque measurements of the pharmaceutical composition of Example 2 with spindle CP-52Z at a rotation speed of 1 rpm

| Sr. No. | Viscosity (mPas) | Torque (%) |
|---------|-----------|------|
| 1 | 58043.70 | 58.5 |
| 2 | 58242.14 | 58.7 |
| 3 | 58142.92 | 58.6 |
| 4 | 58043.70 | 58.5 |
| 5 | 57944.48 | 58.4 |
| 6 | 57746.04 | 58.2 |
| 7 | 57547.60 | 58.0 |
| 8 | 57249.94 | 57.7 |
| 9 | 57051.50 | 57.5 |
| 10 | 56853.06 | 57.3 |
| 11 | 56654.62 | 57.1 |
| 12 | 56654.62 | 57.1 |

TABLE 11-continued

Viscosity and torque measurements of the pharmaceutical composition of Example 2 with spindle CP-52Z at a rotation speed of 1 rpm

| Sr. No. | Viscosity (mPas) | Torque (%) |
|---------|-----------|------|
| 13 | 56158.52 | 56.6 |
| 14 | 56257.74 | 56.7 |

As can be seen from the above Tables 10 and 11, the viscosity of Example 1 was in the range of 64 096 mPas to 72 331 mPas and the viscosity of the composition of Example 2 was in the range of 56 158 mPas to 58 242 mPas.

Example 4—Stability Experiment

The pharmaceutical composition of Example 1 was further tested for its appearance, stability (assay of sirolimus) and viscosity after storage. For this, the pharmaceutical composition was filled into collapsible aluminum tubes, 11 mm×55 mm of size (manufacturer Lindhart), such that the composition comprised 80% of the maximal filling capacity of the aluminum tubes. The tubes were further closed with plastic closures and stored at either 2-8° C. or 25° C. and 60% RH, for 1 month. After being stored for 1 month at the corresponding storage conditions, the composition was pushed out of the collapsible aluminum tubes and tested for its appearance, assay of sirolimus determined by HPLC with Analytical method 1 (c.f. item 1.1) and its viscosity according to the method as described above. Table 12 shows the corresponding results.

TABLE 12

Results after storage

| Time points and conditions | Appearance | Assay (%) | Viscosity (mPas) |
|---------|-----------|------|------|
| Specification | Uniform, lump free, transparent gel | 90.0%-110.0% | Report the results |
| Initial | Complies | 96.4 | 87313 |
| 1 month at 2-8° C. | Complies | 96.0 | 90885 |
| 1 month at 25° C./60% RH | Complies | 94.1 | 85726 |

The pharmaceutical composition of Example 1 was found to be physically and chemically stable for 1 month at 2-8° C. and at 25° C./60% RH as there was no significant difference in assay and viscosity at the 1-month time point compared to initial data.

Example 4.1—Long-Term Stability

The pharmaceutical composition of Example 1 was further tested for its long-term stability (assay of sirolimus) after storage. For this, the pharmaceutical composition was filled into collapsible aluminum as in Example 4 and the tubes were stored at 2-8° C. for 14 months. After being stored, the composition was pushed out of the collapsible aluminum tubes and tested for assay of sirolimus determined by HPLC with Analytical method 1 (c.f. item 1.1). The assay of the sample amounted to 98.0%.

Example 5 In Vitro Release Experiment

The release properties of present Example 1 were compared to the corresponding properties of the 0.4 w/w % sirolimus petrolatum ointment (a known pharmaceutical composition in the prior art) by performing the IVRT as described under item 3.1, wherein this was carried out with 6 replicates each and the corresponding mean value was calculated.

The prior art sirolimus ointment formulation with 0.4 w/w % of sirolimus and 99.6 w/w % of white petrolatum was produced by heating the mixture of these substances at 60° C. in the oven until sirolimus was entirely dissolved in the petrolatum and subsequently stirring the mixture until an ointment-like consistency was achieved.

FIG. 3 shows the cumulative amount of sirolimus released into the receptor fluid from present Example 1 and from the 0.4 w/w % sirolimus petrolatum ointment.

On the one hand, the amount of sirolimus released from the 0.4 w/w % sirolimus petrolatum ointment was around 5 $\mu g/cm^2$ and it stayed constant during the measurement. Hence, sirolimus comprised in the petrolatum ointment was not released from the petrolatum ointment and/or could not permeate through the PES membrane.

On the other hand, the amount of sirolimus released from the gel composition of Example 1 after 0.5 h was around 75 $\mu g/cm^2$ and rose to around 400 $\mu g/cm^2$ after 6 hours. Hence, the gel composition of present Example 1 demonstrated an approximately 80-times better permeation of sirolimus through the release membrane than the conventional 0.4 w/w % sirolimus petrolatum composition.

Example 6—In Vitro Permeability Experiment

The permeability properties of present Example 1 were compared to the corresponding properties of the 0.4 w/w % sirolimus petrolatum ointment as described in Example 5 by performing the IVPT as described under item 3.2, wherein this was carried out with 6 replicates each and the corresponding mean value was calculated.

Table 13 and FIG. 4 show total amounts (mean values and standard errors for 6 replicates) of sirolimus retained in the epidermis and dermis of the skin which had been exposed to the gel composition of Example 1 and to 0.4 w/w % sirolimus petrolatum ointment. The retained amount of sirolimus in the skin from the composition of Example 1 corresponds to 5.42 $\mu g/cm^2$ in the epidermis and to 5.56 $\mu g/cm^2$ in the dermis. In comparison, the retained amount of sirolimus from the petrolatum ointment corresponded to 1.81 $\mu g/cm^2$ in the epidermis and to 2.58 $\mu g/cm^2$ in the dermis. Hence, the amount of retained sirolimus in the epidermis was approximately 3-times higher in present Example 1 than in the 0.4 w/w % sirolimus petrolatum ointment, and approximately 2-times higher in the dermis. Moreover, for the composition of present Example 1, the amount of sirolimus in the epidermis and the dermis was approximately equal. For the 0.4 w/w % sirolimus petrolatum ointment, the amount of sirolimus in the dermis was higher than in the epidermis. Both formulations were not able to deliver sirolimus across the skin into the receptor fluid.

TABLE 13

Amount of sirolimus retained in skin epidermis and dermis after exposing the skin to the 0.4 w/w % sirolimus gel composition of Example 1 and the 0.4 w/w % sirolimus petrolatum ointment for 24 h

| | Mean value | | Standard error | |
|---|---|---|---|---|
| | 0.4 w/w % sirolimus petrolatum ointment | 0.4 w/w % sirolimus gel composition of Example 1 | 0.4 w/w % sirolimus petrolatum ointment | 0.4 w/w % sirolimus gel composition of Example 1 |
| Amount of sirolimus in epidermis ($\mu g/cm^2$) | 1.81 | 5.42 | 0.143 | 0.603 |
| Amount of sirolimus in dermis ($\mu g/cm^2$) | 2.58 | 5.56 | 0.289 | 1.090 |

Hence, the composition of the present invention showed an advantageously higher accumulation of sirolimus in the epidermis and dermis. In other words, with the same dose of sirolimus in the pharmaceutical composition a higher total amount of sirolimus can be retained in the epidermis and dermis. This may lead to reducing the dosing frequency without any negative impact to the therapeutic effect. Further, this may reduce the duration of the treatment and/or the overall drug consumption during said treatment. Also, with reduction of the dosing frequency, compliance of patients by the treatment will improve.

Further, the composition of the present invention showed an advantageously low permeation of sirolimus into the receptor fluid, thereby reducing the risk of permeation of sirolimus into systemic circulation. Thus, the risk for causing systemic side effects is also reduced. Hence, the patients may be treated longer with the sirolimus composition of the present invention, as the time until systemic side effects may occur may be prolonged.

The invention claimed is:

1. A pharmaceutical composition suitable for topical administration comprising:
   a) sirolimus,
   b) solvent,
   c) thickener and
   d) glycol ether
   wherein the content of sirolimus a) is between 0.05 and 5.0 wt. % based on the total weight of the composition,
   wherein the content of thickener c) is between 0.05 and 10.0 wt. % based on the total weight of the composition,
   wherein the content of glycol ether d) is between 0.05 and 10.0 wt. % based on the total weight of the composition,
   wherein solvent b) is selected from the group consisting of propylene glycol, glycerin, alcohol, water or a mixture thereof, and
   wherein thickener c) comprises acrylamide/sodium acryloyldimethyl taurate copolymer.

2. The pharmaceutical composition of claim 1, wherein solvent b) comprises propylene glycol and glycerin.

3. The pharmaceutical composition of claim 1, wherein glycol ether d) is diethylene glycol ethyl ether.

4. The pharmaceutical composition of claim 1, further comprising an antioxidant e).

5. The pharmaceutical composition of claim 4, wherein content of antioxidant e) is between 0.005 and 0.2 wt. %, based on the total weight of the composition.

6. The pharmaceutical composition of claim 4, wherein antioxidant e) is propyl gallate.

7. The pharmaceutical composition of claim 1, wherein the composition is stable at 2 to 8° C. for 1 year.

8. A method of producing a pharmaceutical composition according to claim 1, wherein the method comprises the steps of:

i) providing sirolimus a) and ii) forming said pharmaceutical composition.

9. A method of treating one or more skin diseases or one or more skin manifestations of diseases comprising administering an effective amount of the pharmaceutical composition of claim 1 to a patient in need thereof.

10. The method of claim 9, wherein said one or more skin diseases or one or more skin manifestations of diseases is genodermatoses.

11. The method of claim 9, wherein said one or more skin diseases or one or more skin manifestations of diseases results from vascular conditions, malignant and benign skin tumors, skin manifestations of auto-immune/inflammatory conditions, skin manifestations of infection and infestation, skin manifestations of miscellaneous causes and/or skin manifestations of tuberous sclerosis complex (TSC).

12. The pharmaceutical composition of claim 1, wherein component d) is glycol ether selected from the group consisting of ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monoethyl ether, diethylene glycol mono-n-butyl ether and mixtures thereof, and/or component e) is an antioxidant selected from the group consisting of octyl gallate, dodecyl gallate, propyl gallate (PG) and mixtures thereof.

* * * * *